US011155852B2

(12) United States Patent
Bahle et al.

(10) Patent No.: US 11,155,852 B2
(45) Date of Patent: Oct. 26, 2021

(54) RT-QPCR ANALYSIS OF MICRO-DISSECTED MATERIAL FROM STAINED FFPET SECTION

(71) Applicant: Roche Molecular Systems, Inc., Pleasanton, CA (US)

(72) Inventors: Beatrix Bahle, Oberhausen (DE); Andrea Herold, Murnau (DE); Sabine Lohmann, Penzberg (DE); Sabine Moosmann, Benediktbeuern (DE); Julian Schuster, Penzberg (DE); Monika Singer, Starnberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 184 days.

(21) Appl. No.: 16/042,711

(22) Filed: Jul. 23, 2018

(65) Prior Publication Data

US 2018/0346964 A1   Dec. 6, 2018

Related U.S. Application Data

(63) Continuation of application No. 14/762,422, filed on Jul. 21, 2015, now Pat. No. 10,059,980.

(30) Foreign Application Priority Data

Jan. 24, 2013   (EP) .................................. 13152579
Jan. 22, 2014   (WO) ................. PCT/EP2014/051157

(51) Int. Cl.
  *C12Q 1/6806*   (2018.01)
  *C12Q 1/686*    (2018.01)
  *G01N 1/30*     (2006.01)
  *C12Q 1/6841*   (2018.01)

(52) U.S. Cl.
  CPC .......... *C12Q 1/6806* (2013.01); *C12Q 1/686* (2013.01); *C12Q 1/6841* (2013.01); *G01N 1/30* (2013.01)

(58) Field of Classification Search
  None
  See application file for complete search history.

(56) References Cited

U.S. PATENT DOCUMENTS

| | | |
|---|---|---|
| 2002/0182653 A1 | 12/2002 | Namimatsu |
| 2004/0023207 A1 | 2/2004 | Polansky |
| 2007/0037138 A1 | 2/2007 | Winther |
| 2010/0267571 A1 | 10/2010 | Watanabe |
| 2011/0076262 A1 | 3/2011 | Dennis |
| 2012/0109530 A1* | 5/2012 | Parks ..................... G16B 40/00 702/19 |
| 2012/0159672 A1 | 6/2012 | Alexandrov |

FOREIGN PATENT DOCUMENTS

| | | |
|---|---|---|
| EP | 2711421 | 3/2014 |
| JP | 2004201525 | 7/2004 |
| WO | WO200006780 A1 | 2/2000 |
| WO | 2004019900 | 3/2004 |

OTHER PUBLICATIONS

Seta et al. The Journal of Biological Chemistry 276(48):44405-44412. (Year: 2001).*
Suzuki et al. (2004) BioTechniques 37:542.
Kato et al. (2006) "Extract of DNA concerned with teaching materials of biological education" Bulletin of teacher training research center, Yamagata University p. 39.
Brown, Amanda L., et al., Improved RNA preservation for immunolabeling and laser microdissection, RNA, 2009, 2364-2374, 15.
Buckanovich, Ronald J., et al., Use of immuno-LCM to identify the in situ expression profile of cellular constituents of the tumor microenvironment, Cancer Biology & Therapy, 2006, 635-642, 5.
Cam, Yves, et al., Immunolocalization of acidic and basic fibroblast growth factors during mouse odontogenesis, Int. J. Dev. Biol., 1992, 381-389, 36.
Folkvord, Joy M., et al., Optimization of Immunohistochemical Techniques to Detect Extracellular Matrix Proteins in Fixed Skin Specimens, The Journal of Histochemistry and Cytochemistry, 1989, 105-113, 37:1.
Gilbert, M. Thomas P., et al., The Isolation of Nucleic Acids from Fixed, Paraffin-Embedded Tissues—Which Methods Are Useful When?, PLoS one, 2007, e537, 2(6).
Gjerdrum, Lise Mette MD, et al., The Influence of Immunohistochemistry on mRNA Recovery from Microdissected Frozen and Formalin-Fixed, Paraffin-Embedded Sections, Diagnostic Molecular Pathology, 2004, 224-233, 13(4).
Haishima, Atsuko, et al., Detection of Bcl-2 mRNA and its product in the glomerular podocytes of the normal rat kidney, Experimental and Toxicologic Pathology, 2012, 633-637, 64.
Lohmann, Sabine, et al., Gene expression analysis in biomarker research and early drug development using function tested reverse transcription quantitative real-time PCR assays, Methods, 2013, 10-19, 59.
Macabeo-Ong, Maricris, et al., Effect of Duration of Fixation on Quantitative Reverse Transcription Polymerase Chain Reaction Analyses, Modern Pathology, 2002, 979-987, 15.

(Continued)

*Primary Examiner* — Samuel C Woolwine
(74) *Attorney, Agent, or Firm* — Eric Grant Lee

(57) ABSTRACT

The present invention refers to a method for immunohistochemical staining of a formalin-fixed, paraffin-embedded tissue section comprising the steps of a) providing a solid support, b) mounting the formalin-fixed, paraffin-embedded tissue section onto the solid support, c) removing the paraffin from the formalin-fixed, paraffin-embedded tissue section, d) heating the tissue section mounted on the solid support to retrieve epitopes at 50 to 70° C. for 12 to 24 h, and e) staining the tissue section mounted on the solid support, wherein at least step e) is performed in the presence of 0.5 to 3.0 M sodium chloride. The present invention further refers to a kit for performing the method.

9 Claims, 3 Drawing Sheets

(56) References Cited

OTHER PUBLICATIONS

Figure 1:
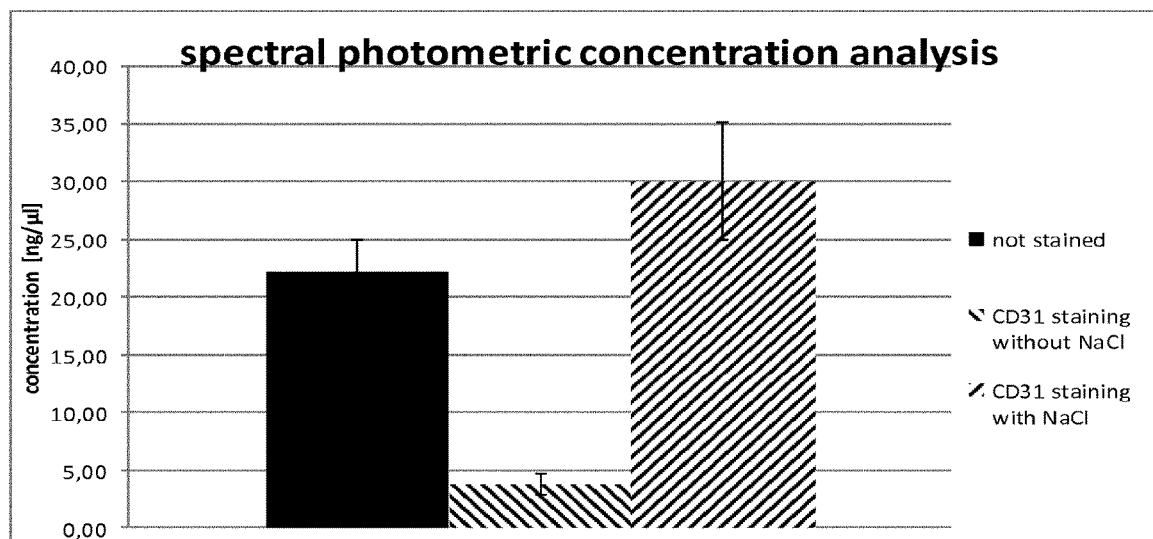

Ramos-Vara, J. A., Technical Aspects of Immunohistochemistry, Veterinary Pathology, 2005, 405-426, 42.
Theophile, Katharina MSC, et al., Amplification of mRNA from Laser-microdissected Single or Clustered Cells in Formalin-fixed and Paraffin-embedded Tissues for Application in Quantitative Real-time PCR, Diagnostic Molecular Pathology, 2008, 101-106, 17(2).

* cited by examiner

A)

B)

RT-QPCR ANALYSIS OF MICRO-DISSECTED MATERIAL FROM STAINED FFPET SECTION

RELATED APPLICATIONS

This patent application is a continuation of U.S. patent application Ser. No. 14/762,422, filed Jul. 21, 2015, which is a U.S. national stage entry of International Patent Application No. PCT/EP2014/051157, filed Jan. 22, 2014, which claims priority from European Patent Application No. EP13152579.2, filed Jan. 24, 2013, the entireties of which are incorporated herein by reference.

BACKGROUND OF THE INVENTION

The present description refers to a method for immuno-histochemical staining of a formalin-fixed, paraffin-embedded tissue section comprising the steps of a) providing a solid support, b) mounting the formalin-fixed, paraffin-embedded tissue section onto the solid support, c) removing the paraffin from the formalin-fixed, paraffin-embedded tissue section, d) heating the tissue section mounted on the solid support to retrieve epitopes at 50 to 70° C. for 12 to 24 h, and e) staining the tissue section mounted on the solid support, wherein at least step e) is performed in the presence of 0.5 to 3.0 M sodium chloride. The present description further refers to a kit for performing the method.

Formalin fixation and paraffin embedding (FFPE) is a well-known procedure for tissue fixation for diagnostic histology and long term storage in clinical routine. Large archives of FFPE tissue (FFPET) samples are used for biomarker discovery studies as well as early clinical studies. Furthermore, FFPET samples can be used for isolation of RNA which can further be applied in gene expression analyses. Although, RNA from FFPET samples shows a high degree of degradation, it is still sufficient for RT-qPCR analyses provided that a sufficient amount of material is used for RNA isolation. Such analyses can be used to generate a first biomarker hypothesis and simply for hypothesis testing (Lohmann et al, Methods. 2013 January; 59(1)).

To be able to separate blood vessels and tumor cell nests from FFPE tissue sections and perform RT-qPCR analysis, we combined the following technologies: laser capture micro-dissection (LCM) from FFPET after immuno-histochemical staining with RT-qPCR analysis after pre-amplification of the cDNA.

The challenges the skilled person is faced with when combining LCM from IHC-stained FFPET sections followed by RT-qPCR analysis is the very limited amount of material after LCM, RNA degradation after fixation of the sample tissue and in addition the RNA degradation during the immuno-histological staining procedure. The classical staining procedure includes epitope retrieval (e.g. HIER protocol at 98° C.) and incubation times with buffers that cannot be produced under RNAse free conditions (antibody solution, washing buffers, dyes). The described RNA degradation in combination with the very limited amount of material after LCM is the major problem of this workflow if the RNA is intended to be used in RT-qPCR analyses. The degradation of RNA lead to unreliable results in gene expression analyses following LCM, e.g. the ratio between a biomarker of interest and a reference gene. mRNA stability is gene-specific and therefore they are degrading to a different extend, leading to wrong results in relative quantification for gene expression analysis.

To overcome this problem of RNA degradation, different procedures have been established to keep the degradation to a minimum. The majority of publications for example use Fresh Frozen (FF) tissue which has the advantage of less degradation processes when used for RT-qPCR analyses. The major drawback, however, is the fact that FF tissue is a largely limited source as compared to FFPET (Buckanovich et al., Cancer Biol Ther. 2006 June; 5(6):635-42; Gjerdrum et al., Diagn Mol Pathol 2004 (13), p. 224-233) It is often difficult to obtain a sufficient amount of FF tissue for performing a study leading to statistically significant results. Furthermore the clinical sample material available for retrospective testing is typically FFPET.

Therefore, a main focus in this field was the development of techniques using FFPET in combination with LCM and RT-qPCR analyses minimizing the RNA degradation. Ultrafast staining procedures for FFPET-sections were developed to minimize RNA degradation during the staining. However, analyzing the RNA from such microdissected, ultra-fast stained FFPET-sections showed that after antibody incubation with very short incubation periods (2×5 min) still approximately 90% of the RNA was degraded as compared to a simple histological stain (Hematoxylin) (Gjerdrum et al., Diagn Mol Pathol 2004 (13)). In addition, ultra-fast staining protocols are not applicable to all antibodies as some need several hours to overnight incubation (Brown et al., RNA Journal 2009 (15), p. 2364-2374). Such long term incubation procedures lead to massive RNA degradation, such that gene expression analyses are simply impossible.

Therefore, the object of the present description is to provide an improved staining technique for FFPET-sections subsequently used for RNA isolation, wherein the improved staining technique leads to a yield and quality of the isolated RNA from FFPET-sections sufficient for RNA analyses, such as gene expression analyses.

SUMMARY OF THE INVENTION

It was found that high salt concentrations of 0.5 to 3.0 M sodium chloride in the staining method described herein applied to tissue sections mounted on the solid support prevent degradation of RNA isolated subsequently from the tissue sections. The method according to the description is suitable for staining procedures, where RNA is isolated after the staining and where high quality RNA is required, such as for gene expression analyses.

The present description thus refers to a method for immuno-histochemical staining of a formalin-fixed, paraffin-embedded tissue section comprising the steps of a) providing a solid support, b) mounting the formalin-fixed, paraffin-embedded tissue section onto the solid support, c) removing the paraffin from the formalin-fixed, paraffin-embedded tissue section, d) heating the tissue section mounted on the solid support to retrieve epitopes at 50 to 70° C. for 12 to 24 h, and e) staining the tissue section mounted on the solid support, wherein at least step e) is performed in the presence of 0.5 to 3.0 M sodium chloride.

Furthermore, the present description refers to a kit for performing the method as described herein, wherein the kit comprises a) a solid support coated with poly-lysine, b) a solution for epitope retrieval, and c) a solution for immuno-histochemical staining comprising sodium chloride in a concentration of 0.5 to 3.0 M.

FIGURES

FIG. 1: The figure shows the result of a spectral photometric concentration analysis of isolated RNA. Depicted is the median+/−standard deviation of the RNA-concentrations from extracts isolated from unstained FFPET sections (not stained), isolated from FFPET sections stained with CD31 in the absence of sodium chloride (without NaCl) and isolated from FFPET sections stained with CD31 in the presence of sodium chloride (with NaCl). Data were obtained from three independent replicates each.

Figure 2:
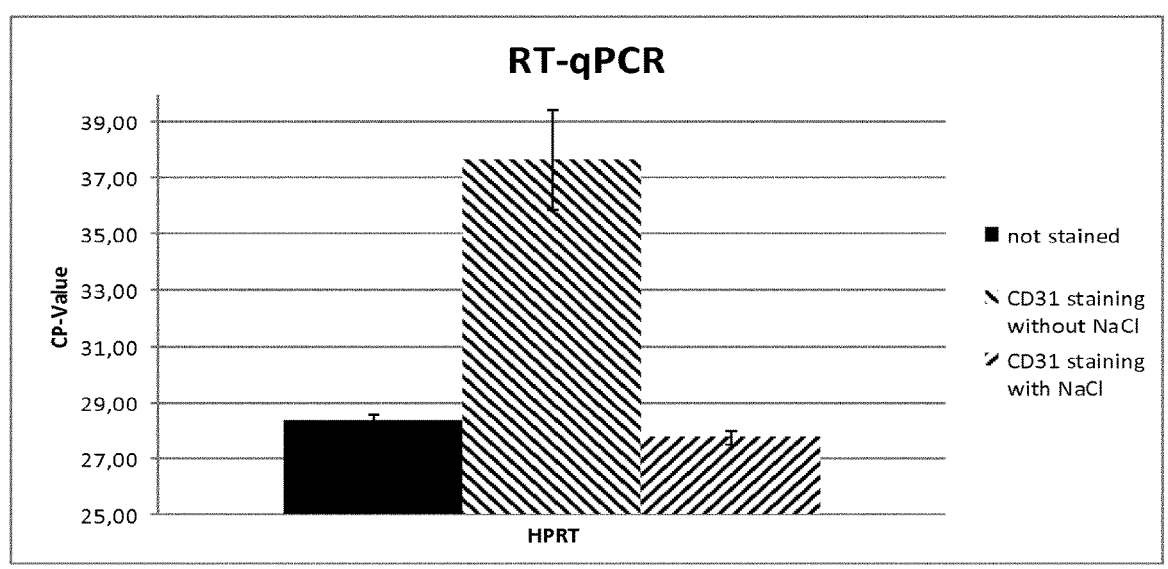

FIG. 2: The figure shows the Cp-values of an RT-qPCR analysis of the reference gene HPRT (hypoxanthine-guanine phosphoribosyltransferase). Depicted is the median+/−standard deviation of the Cp-values from RT-qPCR experiments. RNA was isolated from unstained FFPET sections (not stained), isolated from FFPET sections stained with CD31 in the absence of sodium chloride (without NaCl) and isolated from FFPET sections stained with CD31 in the presence of sodium chloride (with NaCl). Data were obtained from three independent replicates each.

Figure 3:
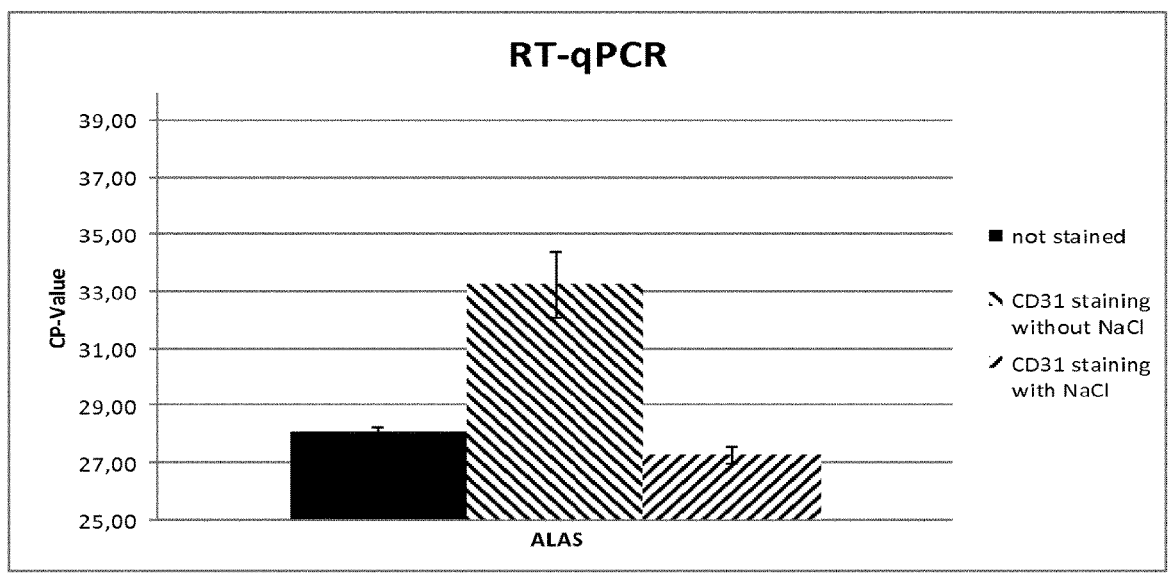

FIG. 3: The figure shows the Cp-values of an RT-qPCR analysis of the reference gene ALAS1 (delta-aminolevulinate synthase 1). Depicted is the median+/−standard deviation of the Cp-values from RT-qPCR experiments. RNA was isolated from unstained FFPET sections (not stained), isolated from FFPET sections stained with CD31 in the absence of sodium chloride (without NaCl) and isolated from FFPET sections stained with CD31 in the presence of sodium chloride (with NaCl). Data were obtained from three independent replicates each.

Figure 4:
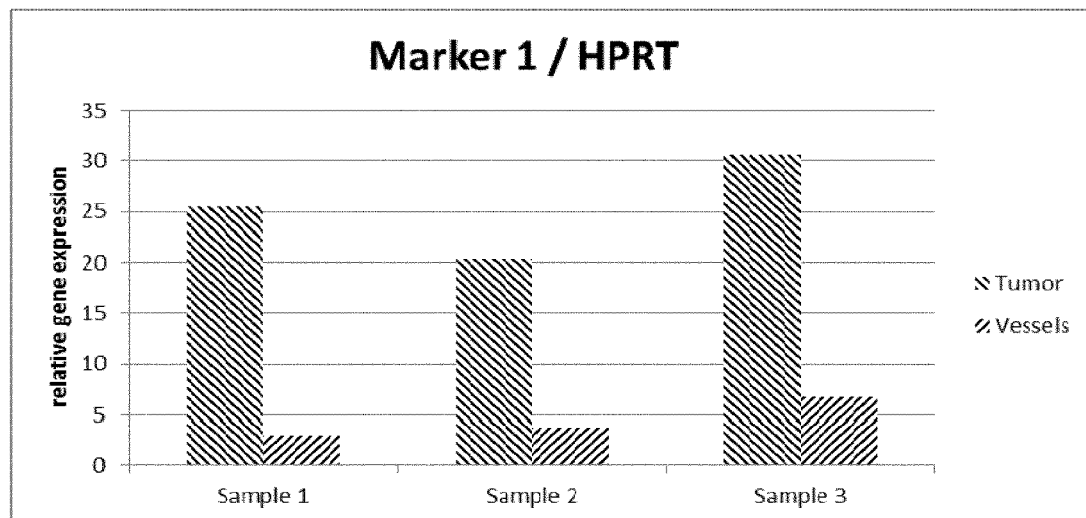
Figure 4:
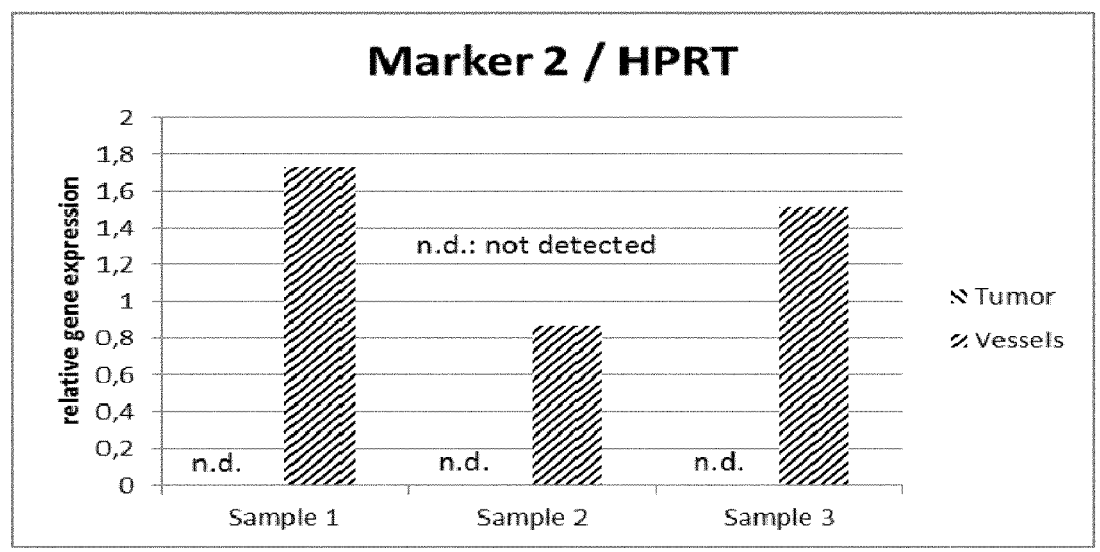

FIG. 4: The figure shows the expression of Marker 1 and Marker 2 normalized to the reference gene HPRT, respectively. Depicted is the relative gene expression of Marker 1 and Marker 2 from microdissected tumor cells and vessel cells, respectively. Experiments were performed in duplicates.

DETAILED DESCRIPTION OF THE INVENTION

The following definitions are set forth to illustrate and define the meaning and scope of various terms used herein.

The terms "a", "an" and "the" generally include plural referents, unless the context clearly indicates otherwise.

The term "about" as used herein in conjunction with a numerical value modifies that value by extending the boundaries above and below the values. In general, the term "about" modifies a numerical value above and below the stated value by a variance of 5% higher or lower. For example a value of "about 100" means a range of "95 to 105".

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification.

The term "antibody" as used herein refers to a complete immunoglobulin, such as an IgA, IgD, IgE, IgG or IgM or to a fragment of an antibody, such as a Fab, Fv or Fc or a fused antibody, a fused antibody fragment or any other derivative of an antibody. The term "labeled antibody" refers to an antibody that is labeled with an enzyme, a fluorescent dye, a chemiluminescent substance, biotin, avidin or a radioisotope.

The term "epitope" refers to an antigenic region of a compound, such as a protein, a carbohydrate or a lipid. The antigenic region typically consists of 5 to 8 amino acids. The epitope is specifically recognized by the antigen binding sites of the respective antibody.

The term "fixed tissue or cell" is used herein as known to the expert skilled in the art and refers to biological tissue or cells which are preserved from decay by chemical fixation methods. Such methods prevent autolysis or putrefaction within such biological tissue or cells. Fixation terminates biochemical reactions and increases the mechanical stability of the treated tissue.

The term "immuno-histochemistry" and "immuno-histochemical" refers to a technique for detecting the presence of an antigen with an antibody capable of specifically binding to said antigen in histological samples. The detection of the antibody-antigen complex occurs usually by a chromogenic reaction with an enzyme-labeled antibody or by a fluorescent labeled antibody.

The term "macrodissection" as used herein refers to the process of scratching an area of interest from a tissue section mounted on a solid support, such as a microscope slide, by using a tool such as a scalpel or a spatula.

The term "membrane slide" as used herein refers to solid supports or microscope slides for use in Laser Capture Microdissection (LCM). For microdissection glass slides covered with a membrane or frame slides that consist of a metal frame which can be covered with various membranes can be used. The material of the membrane can be selected from the group consisting of polyphenylene sulfide (PPS), polyethylene naphthalate (PEN), polyester (POL) and fluorocarbon (FLUO).

The term "microdissection" as used herein refers to the process of cutting and separating one or more specific cells or an area of interest from a tissue sample. Microdissection can for example be performed using laser capture microdissection (LCM) by cutting the relevant area with a laser.

The term "nucleic acid" generally refers to DNA or RNA, whether it is a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3' or 5' overhangs and as such are not required or assumed to be completely double-stranded over their entire length. Furthermore, the term nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoroamidates and phosphorotiester linkages between nucleotides to prevent degradation; methylation; and modified bases such as deoxyInosine, 5-Bromo dU, deoxyUridine, 2-Aminopurine, dideoxyCytidine, 5-Methyl dC, locked nucleic acids (LNA's), Iso-dC and -dG bases, 2'-O-Methyl RNA bases and Fluorine Modified Bases.

The term "poly-lysine" refers to a molecule that contains up to several hundreds of repeating units and is suitable for increasing the affinity between a sample, such as a tissue section, and the membrane slide onto which the sample is mounted. A poly-lysine according to the description is poly-L-lysine. Poly-L-lysine according to the description has a molecular weight from 70 to 300 kDa. Poly-L-lysine can be digested by proteases. Another poly-lysine according to the description is for example poly-D-lysine. Poly-D- lysine according to the description has a molecular weight from 70 to 300 kDa. Poly-D-lysine is resistant to protease digestion.

The term "qPCR" generally refers to the PCR technique known as real-time quantitative polymerase chain reaction, quantitative polymerase chain reaction or kinetic polymerase chain reaction. This technique simultaneously amplifies and quantifies target nucleic acids using PCR wherein the quantification is by virtue of an intercalating fluorescent dye or sequence-specific probes which contain fluorescent reporter molecules that are only detectable once hybridized to a target nucleic acid.

The term "RNA" is used herein as known to the expert skilled in the art and refers to pre-mRNA, pre-mRNA transcripts, mRNA, transcript processing intermediates, mature mRNA used for translation and transcripts from a gene or genes, or nucleic acids derived therefrom. Transcript processing includes processes such as splicing, editing, modifying and degrading. mRNA including samples include, but are not limited to mRNA, mRNA transcripts of the gene or genes, cDNA originating from mRNA using reverse transcription, RNA transcribed from amplified DNA, cRNA transcribed from cDNA, DNA amplified from the genes, and the like.

The term "solid support" is used herein as known to the expert skilled in the art and refers to any solid material, having a surface area to which tissue sections can be mounted or attached. The support can be a combination of materials such as plastic on glass, carbon on glass, and the like. In a specific embodiment, the solid support can be a "membrane slide" as defined above.

The present description refers to a method for immunohistochemical staining of a formalin-fixed, paraffin-embedded tissue section comprising the steps of a) providing a solid support, b) mounting the formalin-fixed, paraffin-embedded tissue section onto the solid support, c) removing the paraffin from the formalin-fixed, paraffin-embedded tissue section, d) heating the tissue section mounted on the solid support to retrieve epitopes at 50 to 70° C. for 12 to 24 h, and e) staining the tissue section mounted on the solid support, wherein at least step c) is performed in the presence of 0.5 to 3.0 M sodium chloride. As known by the skilled person, the term "sodium chloride" and empirical formula "NaCl" can be used interchangeably within the present description. In one embodiment, the sodium chloride is present in a concentration of 1.5 to 2.5 M. In a more specific embodiment, the sodium chloride is present in a concentration of about 1.8 to 2.2 M. In an even more specific embodiment, the sodium chloride is present in a concentration of about 2 M.

It was found that, as can be taken also from the Examples, using high salt concentrations of 0.5 to 3.0 M sodium chloride in at least the step of staining the tissue section mounted on the solid support, prevent RNA isolated subsequently from the FFPET section from degradation. Thus, the method according to the description using high salt concentrations of 0.5 to 3.0 M sodium chloride is suitable for staining procedures, where RNA is isolated after the staining and where high quality RNA is required, such as for RT-qPCR experiments.

In one embodiment, the method further comprises the steps of f) dissecting from the stained tissue section mounted on the solid support an area of interest, g) isolating RNA from the area of interest, h) analyzing the isolated RNA. In one embodiment, analyzing the isolated RNA comprises any method known in the art, such as RNA profiling, RNA sequencing and gene expression analyses. Thus, the method according to the description can be used to isolate RNA with increased quality from FFPET section such that the results of basically any subsequent method can be improved significantly by applying the RNA stabilization in FFPET sections as described herein.

In another embodiment, the method further comprises the steps of f) dissecting from the stained tissue section mounted on the solid support an area of interest, g) isolating RNA from the area of interest, h) reverse transcribing the isolated RNA into cDNA, i) amplifying and quantifying the cDNA. In one embodiment, steps h) and i) are performed as one-step PCR. In another embodiment, steps h) and i) are performed as two-step PCR. In a specific embodiment, the step of amplifying and quantifying the cDNA is performed by Real Time PCR.

In one embodiment, the solid support is coated with poly-L-lysine. In another embodiment, the solid support is coated with poly-D-lysine. In a specific embodiment, the solid support is coated with poly-L-lysine or poly-D-lysine by applying a solution of poly-L-lysine or poly-D-lysine to the solid support. In one embodiment, the solid support is incubated 15 to 45 min after the application of the solution of poly-L-lysine or poly-D-lysine. In a specific embodiment, the solid support is incubated 30 min after the application of the solution of poly-L-lysine or poly-D-lysine. In a specific embodiment, the solution has a concentration of 0.05 to 2% of poly-L-lysine or poly-D-lysine. In a more specific embodiment, the solution has a concentration of 0.1% of poly-L-lysine or poly-D-lysine. In another specific embodiment, the poly-L-lysine or poly-D-lysine has a molecular weight from 70 to 300 kDa. In another specific embodiment, the solid support is a membrane slide.

In one embodiment, the solid support is treated with 3-aminopropyltriethoxysilane (APES). Such silanization can be performed to functionalize the surface of the solid support with alkoxysilane molecules resulting in an increased attachment of the tissue sections on the solid support.

In one embodiment, the formalin-fixed, paraffin-embedded tissue section mounted on the solid support has a thickness of 2 to 10 μm. In a specific embodiment, the formalin-fixed, paraffin-embedded tissue section mounted on the solid support has a thickness of 4 to 6 μm. In a more specific embodiment, the formalin-fixed, paraffin-embedded tissue section mounted on the solid support has a thickness of about 5 μm.

In one embodiment, removing the paraffin is performed by incubating the tissue section mounted on the solid support in xylol. Subsequently, the tissue section mounted on the solid support is rehydrated in a series of decreasing concentration of ethanol, e.g. several seconds in each of 100%, 96% and 70% ethanol, followed by 2×1 min in water.

In order to maximally prevent the RNA from degradation, a low-temperature heat induced epitope retrieval (LT-HIER) protocol was established. Epitope retrieval was found to provide the best results, when the tissue section mounted on the solid support was heated at 60° C. for 16 h at pH8. In one embodiment, sodium chloride can be present in a concentration of 2 M in the solution for epitope retrieval.

Thus, in one embodiment, heating of the tissue section mounted on the solid support is performed in the presence of 0.5 to 3.0 M sodium chloride. In a specific embodiment, heating of the tissue section mounted on the solid support is performed in the presence of 1.5 to 2.5 M sodium chloride. In another specific embodiment, heating of the tissue section mounted on the solid support is performed in the presence of 1.8 to 2.2 M sodium chloride. In an even more specific embodiment, heating of the tissue section mounted on the solid support is performed in the presence of about 2.0 M sodium chloride.

In one embodiment, heating of the tissue section mounted on the solid support is performed at 50 to 70° C. In a specific embodiment, heating of the tissue section mounted on the solid support is performed at 55 to 65° C. In another specific embodiment, heating of the tissue section mounted on the solid support is performed at 58 to 62° C. In an even more specific embodiment, heating of the tissue section mounted on the solid support is performed at about 60° C.

In one embodiment, heating of the tissue section mounted on the solid support is performed for 12 to 24 h. In a specific embodiment, heating of the tissue section mounted on the solid support is performed for 14 to 18 h. In a more specific embodiment, heating of the tissue section mounted on the solid support is performed for 15 to 17 h. In an even more specific embodiment, heating of the tissue section mounted on the solid support is performed for about 16 h.

In one embodiment, heating of the tissue section mounted on the solid support is performed at pH 5 to 9. In a specific embodiment, heating of the tissue section mounted on the solid support is performed at pH 7.5 to 8.5. In a more specific embodiment, heating of the tissue section mounted on solid support is performed at pH 7.8 to 8.2. In a specific embodiment, heating of the tissue section mounted on the solid support is performed at a pH value of about 8.

In a specific embodiment, heating of the tissue section mounted on the solid support is performed at about 60° C. for about 16 h at a pH value of about 8. In one embodiment, sodium chloride can be present in a concentration of 2 M in the solution for epitope retrieval.

After the heating step, the tissue section mounted on the solid support is cooled in buffer with a concentration of 0.5 to 3.0 M sodium chloride. In a specific embodiment, the buffer is TBS-T. In another specific embodiment, sodium chloride is present in a concentration of about 2 M.

In one embodiment, the staining of the tissue section mounted on the solid support comprises an antibody based staining. In a specific embodiment the antibody-based staining comprises the use of a primary antibody and a secondary antibody. In a more specific embodiment, the primary antibody is a CD31-binding antibody. In an even more specific embodiment, the primary antibody is CD31 monoclonal antibody (mAb) Clone JC70. In a specific embodiment the secondary antibody is an anti-mouse antibody. In a more specific embodiment, the secondary antibody is covalently bound to an enzyme capable of transforming a substrate into one or more products. In an even more specific embodiment, the secondary antibody is covalently bound to horseradish peroxidase (HRP).

Antibody based staining was found to provide the best results, when the tissue section mounted on the solid support was incubated with the primary antibody at 37° C. for 1 h, wherein sodium chloride was present in a concentration of 2 M. In one embodiment, incubation of the tissue section mounted on the solid support with the primary antibody is performed at 34 to 40° C. In one embodiment, incubation of the tissue section mounted on the solid support with the primary antibody is performed for 0.5 to 1.5 h. In one embodiment, incubation of the tissue section mounted on the solid support with the primary antibody is performed in presence of 0.5 to 3.0 M sodium chloride. In a specific embodiment, incubation of the tissue section mounted on the solid support with the primary antibody is performed at about 37° C. In another specific embodiment, incubation of the tissue section mounted on the solid support with the primary antibody is performed for about 1 h. In yet another specific embodiment, incubation of the tissue section mounted on the solid support with the primary antibody is performed in the presence of about 2.0 M sodium chloride. In a more specific embodiment, incubation of the tissue section mounted on the solid support with the primary antibody is performed at about 37° C. for about 1 h, wherein sodium chloride is present in a concentration of about 2 M.

Incubation with the secondary antibody was performed at room temperature for 2 h in a humidity chamber, wherein sodium chloride was present in a concentration of 2 M. In one embodiment, incubation of the tissue section mounted on the solid support with the secondary antibody is performed at 16 to 24° C. In one embodiment, incubation of the tissue section mounted on the solid support with the secondary antibody is performed for 1.5 to 2.5 h. In one embodiment, incubation of the tissue section mounted on the solid support with the secondary antibody is performed in the presence of 0.5 to 3.0 M sodium chloride. In a specific embodiment, incubation of the tissue section mounted on the solid support with the secondary antibody is performed at about 20° C. In another specific embodiment, incubation of the tissue section mounted on the solid support with the secondary antibody is performed for about 2 h. In yet another specific embodiment, incubation of the tissue section mounted on the solid support with the secondary antibody is performed in the presence of about 2.0 M sodium chloride. In a more specific embodiment, incubation of the tissue section mounted on the solid support with the secondary antibody is performed at about 20° C. for about 2 h, wherein sodium chloride is present in a concentration of about 2 M.

In one embodiment, the staining of the tissue section mounted on the solid support further comprises an enzyme-substrate reaction catalyzed by an enzyme covalently bound to the secondary antibody. Thus, in a specific embodiment, the staining comprises the use of a labeled antibody. The enzyme can be selected from the group consisting of peroxidases and alkaline phosphatases. Peroxidases, such as HRP, are capable of transforming substrates selected from the group consisting of 3,3'-diaminobenzidin (DAB), 3-amino-9-ethylcarbazol (AEC), 4-chlor-1-naphthol (CN) and p-phenylendiamin dihydrochloride. Alkaline phosphatases are capable of transforming substrates selected from the group consisting of naphthol as-mx-phosphate, hexazotizing triamino-tritolyl-methanchloride, naphthol AS-BI-phosphate, naphthol AS-TR-phosphate, 5-brom-4-chlor-3-indoxylphosphat (BCIP), nitroblue-tetrazolium (NBT), iodnitrotetrazolium-violett (INT), Fast Red TR, Fast Red LB, Fast Blue BB and Fast Garnet GBC.

In a specific embodiment, the enzyme capable of transforming the substrate is HRP. In a specific embodiment, the substrate transformed by HRP is DAB. In one embodiment, the DAB staining is performed in the presence of 0.5 to 3.0 M sodium chloride. In a specific embodiment, sodium chloride is present in a concentration of about 2 M. In one embodiment, the DAB staining was performed for 5-20 min at room temperature. In a specific embodiment, the DAB staining was performed for about 10 min at room temperature.

In one embodiment, the solid support is a membrane slide. In a specific embodiment, the solid support is a membrane slide suitable for LCM. In a specific embodiment, the membrane slide is a polyethylene naphthalate membrane slide. It has been shown that commercially available membrane slides, such as polyethylene naphthalate membrane slides are not suitable for the method according to the present description. The commercially available membrane slides do not provide enough adhesion to the FFPET sections during the step of heating the tissue sections mounted on the coated membrane slides to retrieve epitopes. In order to improve the adhesion between the membrane slides and the FFPET sections during the step of heating, the membrane slides were coated with poly-L-lysine which increased the adhesion between the membrane slides and the FFPET sections in a way that the FFPET sections were stably attached to the membrane slides.

In one embodiment, the step of dissecting from the stained tissue section mounted on the solid support an area of interest comprises microdissecting or macrodissecting an area of interest. In a specific embodiment, the step of microdissecting comprises the process of cutting and separating one or more specific cells or an area of interest from a tissue sample. Microdissection can for example be performed using laser capture microdissection (LCM) by cutting the relevant area with a laser. In a specific embodiment, the step of macrodissecting comprises the process of scratching an area of interest from a tissue section mounted on a solid support, such as a microscope slide, by using a tool such as a scalpel or a spatula.

In the method according to the description, LCM was used on the stained FFPET section attached to the membrane slide to cut an area of interest from the tissue section. The area of interest was subsequently used for RNA isolation. In one embodiment, the area of interest has a size of 0.5-5 $mm^2$. In a specific embodiment, the area of interest has a size of 1-2 $mm^2$. RNA was isolated from the area of interest using methods well known in the art, such as by using the High Pure FFPET RNA Isolation Kit® (Roche Diagnostics GmbH). The isolated RNA was subsequently reverse transcribed in order to obtain cDNA. Due to limited amount of cDNA and to provide sufficient nucleic acid for a qPCR experiment, a preamplification step can be performed on the cDNA prior to amplification by qPCR. Thus, in one embodiment, the method according to the description further comprises the steps of f) microdissecting from the stained tissue section mounted on the coated membrane slide an area of interest, g) isolating RNA from the area of interest, h) reverse transcribing the isolated RNA into cDNA, i) preamplifying the cDNA, and j) amplifying and quantifying the preamplified cDNA. In a specific embodiment, the step of amplifying and quantifying the preamplified cDNA is performed by Real Time PCR.

In a specific embodiment, the present description refers to a method for immuno-histochemical staining of a formalin-fixed, paraffin-embedded tissue section comprising the steps of a) providing a membrane slide coated with poly-L-lysine, b) mounting the formalin-fixed, paraffin-embedded tissue section onto the membrane slide, c) removing the paraffin from the formalin-fixed, paraffin-embedded tissue section by incubating the tissue section mounted on the solid support in xylol, d) heating the tissue section mounted on the membrane slide to retrieve epitopes at about 60° C. for about 16 h, and e) staining the tissue section mounted on the membrane slide by use of a labeled antibody, f) microdissecting from the stained tissue section mounted on the membrane slide an area of interest having a size of 1-2 $mm^2$, g) isolating RNA from the area of interest, h) reverse transcribing the isolated RNA into cDNA, i) amplifying and quantifying the cDNA, wherein at least step e) is performed in the presence of about 2 M sodium chloride and wherein the step of amplifying and quantifying the cDNA is performed by Real Time PCR.

The present description further refers to a kit for performing the method as described above. Thus, the present description further refers to a kit for performing a method for immuno-histochemical staining of a formalin-fixed, paraffin-embedded tissue section comprising the steps of a) providing a solid support, b) mounting the formalin-fixed, paraffin-embedded tissue section onto the solid support, c) removing the paraffin from the formalin-fixed, paraffin-embedded tissue section, d) heating the tissue section mounted on the solid support to retrieve epitopes at 50 to 70° C. for 12 to 24 h, and e) staining the tissue section mounted on the solid support, wherein at least step e) is performed in the presence of 0.5 to 3.0 M sodium chloride. In one embodiment, the sodium chloride is present in a concentration of 1.5 to 2.5 M. In a more specific embodiment, the sodium chloride is present in a concentration of about 1.8 to 2.2 M. In an even more specific embodiment, the sodium chloride is present in a concentration of about 2 M.

In one embodiment, the method performed with the kit further comprises the steps of f) dissecting from the stained tissue section mounted on the solid support an area of interest, g) isolating RNA from the area of interest, h) reverse transcribing the isolated RNA into cDNA, i) amplifying and quantifying the cDNA. In one embodiment, steps h) and i) are performed as one-step PCR. In another embodiment, steps h) and i) are performed as two-step PCR. In a specific embodiment, the step of amplifying and quantifying the cDNA is performed by Real Time PCR.

In one embodiment, the kit for performing the method according to the description comprises a) a solid support, b) a solution for epitope retrieval, and c) a solution for immuno-histochemical staining comprising sodium chloride in a concentration of 0.5 to 3.0 M. In another embodiment, the kit for performing the method according to the description comprises a) a membrane slide coated with poly-lysine, b) a solution for epitope retrieval, and c) a solution for immuno-histochemical staining comprising sodium chloride in a concentration of 0.5 to 3.0 M. In a specific embodiment the kit further comprises all reagents necessary for performing reverse transcription from RNA into cDNA, and amplification and quantitation of the cDNA. In another specific embodiment the kit comprises all reagents necessary for performing reverse transcription from RNA into cDNA, preamplifying the cDNA, and amplifying and quantifying the preamplified cDNA.

The following examples 1-3 are provided to aid the understanding of the present invention, the true scope of which is set forth in the appended claims. It is understood that modifications can be made in the procedures set forth without departing from the spirit of the invention.

Example 1

Coating of Membrane Slides with Poly-L-Lysine

The PEN membrane slides (MicroDissect GmbH) were covered with about 1 ml poly-L-lysine solution (0.1% w/v, Sigma-Aldrich Chemie GmbH) and incubated for 30 min in a humidity chamber at room temperature. The poly-L-lysine solution was removed by performing powerful shaking. Subsequently the PEN membrane slides were dried overnight under UV-Light.

Observed Results (not Shown):

Coating of the PEN membrane slides with poly-L-lysine lead to an increased attachment of the tissue section to the membrane slide when applied to low-temperature heat induced epitope retrieval (LT-HIER, 60° C., 16 h, pH 8). Membrane slides coated with poly-L-lysine: 0 of 3 tissue sections detached from the slide. Membrane slides without poly-L-lysine: 3 of 3 tissue sections detached from the slide.

Example 2

CD31-Staining without/with 2 M Sodium Chloride

FFPET sections of tumor samples were used for antibody-based staining and subsequent RNA isolation. The following description only refers to the procedure performed to stain the FFPET sections in presence of 2 M sodium chloride. For experiments without sodium chloride, exactly the same procedure was performed with the following differences: 1) Sodium chloride was omitted in the staining procedure, 2) the incubation with the secondary antibody was performed for 30 min (instead of 2 h with 2 M sodium chloride). The high salt concentration required an increased incubation time due to reduced binding efficiency of the secondary antibody.

5 μm FFPET sections were attached on poly-L-Lysine-coated PEN membrane slides and dried overnight in dust free environment. Subsequently, the FFPET sections were incubated for 5 min in 3% $H_2O_2$ (AppliChem GmbH). Then the FFPET sections were washed 2 min in $H_2O$ PCR-Grade. Incubation of the sections was performed for 16 h at 60° C. in Epitope Retrieval Solution (Leica Microsystems GmbH). Afterwards, CD31-staining with EnVision™ anti-Mouse (DAKO GmbH) was performed. Sodium chloride (molecular biology grade, Sigma-Aldrich Chemie GmbH) was dissolved in all staining reagents (Protein Block serum free (DAKO GmbH), primary and secondary antibody, DAB-Chromogen (Thermo Fisher Scientific GmbH) and Tris-Buffered Saline and Tween 20 (TBS-T) wash buffer). The final concentration of sodium chloride was about 2 M. The sections were cooled to room temperature for 5 min in TBS-T/sodium chloride. Sections were incubated with 100 μl protein block/sodium chloride for 5 min in the humidity chamber. Subsequently, the liquid was shaken off the sections and 100 μl primary antibody/sodium chloride was added, covered with parafilm and incubated 1 h at 37° C. The sections were washed 2×2 min with TBS-T/sodium chloride and afterwards 100 μl secondary antibody/sodium chloride was added and incubated 2 h at room temperature in the humidity chamber. After washing 2×2 min with TBS-T/sodium chloride, 100 μl OF DAB-Chromogen/sodium chloride was added and incubated 5-10 min at room temperature in the humidity chamber. The sections were washed 2 min with TBS-T/sodium chloride. Subsequently, the sections were washed 2 min with $H_2O$ (PCR-Grade). The stained sections were dissected and total RNA was isolated (High Pure Paraffin RNA Kit, Roche Diagnostics GmbH). RNA concentration was determined by spectral photometric analysis (NanoDrop ND 1000 Spectralphotometer). RNA was transcribed into cDNA by the methods well known in the art. cDNA was pre-amplified. Subsequently, amplification was performed by real-time PCR (LightCycler® Platform).

Observed Results:

The RNA-concentrations of the CD31-stained sections without sodium chloride are significantly lower as compared to the unstained sections. The RNA concentrations of the CD31-stained FFPET sections with sodium chloride do not differ significantly from the unstained sections (see FIG. 1).

The Cp-values (reference gene HPRT) of the CD31-stained sections without sodium chloride are significantly higher as compared to the unstained sections. The Cp-Values of the CD31-stained FFPET sections with sodium chloride do not differ significantly from the unstained sections (see FIG. 2).

The Cp-values (reference gene ALAS1) of the CD31-stained sections without sodium chloride are significantly higher as compared to the unstained sections. The Cp-Values of the CD31-stained FFPET sections with sodium chloride do not differ significantly from the unstained sections (see FIG. 3).

Example 3

Gene Expression Analysis of Two Markers from CD31-Stained FFPET Sections

The example shows the suitability of RNA isolated from CD-31-stained FFPET sections with the method according to the description for gene expression experiments. The method described in Example 2 was applied to FFPET sections from three independent tumor samples. The samples were mounted on membrane slides. Areas of interest (tumor and vessels) were microdissected using successive laser capture micro-dissection. Data on the expression of two different markers (Marker 1 and Marker 2) in tumor dissections and vessel dissections, respectively, were obtained by analyzing the isolated RNA. Experiments were performed in duplicates. The RNA was transcribed into cDNA using methods well known in the art. The cDNA was pre-amplified to obtain sufficient starting material and to increase sensitivity. The pre-amplified cDNA was finally analyzed in duplicates using Real Time PCR. Relative expression of Marker 1 and Marker 2 was obtained by normalizing the expression of Marker 1 and Marker 2 to the reference gene HPRT, respectively.

Observed Results:

In consistence with previous experiments performed on unstained tumor samples (data not shown), FIG. 4 shows data regarding the pattern of the relative expression of Marker 1 and Marker 2 obtained from three independent CD31-stained tumor samples. FIG. 4 A) shows that Marker 1 is expressed to a larger extend in tumor cells as compared to vessel cells. Furthermore, FIG. 4 B) shows that Marker 2 is expressed to a larger extend in vessel cells as compared to tumor cells. In this case, the expression in tumor cells is very low as compared to the vessel cells such that an expression cannot be detected (not detected=n.d.). As the analysis of the unstained tumor samples (data not shown) could be reproduced, it can be concluded that the staining method according to the description is not significantly influencing the RNA quality in a way that the results are affected. Consequently, with the method according to the description, RNA degradation can be minimized such that the quality of RNA from FFPET samples is sufficient for gene expression analysis or any other method for analyzing RNA.

The invention claimed is:

1. A kit for performing immuno-histochemical staining of a formalin-fixed, paraffin-embedded tissue section, the kit comprising:
   (a) a solid support coated with poly-lysine, wherein the solid support is a membrane slide,
   (b) an epitope retrieval solution, and
   (c) a staining solution comprising sodium chloride, wherein the sodium chloride is present in a concentration of 0.5 to 3.0 M.

2. The kit of claim 1, wherein the kit further comprises reagents for performing reverse transcription from RNA into cDNA, and amplification and quantitation of the cDNA.

3. The kit of claim 1, wherein the poly-lysine is poly-L-lysine.

4. The kit of claim 1, wherein the sodium chloride present in a concentration of 1.5 to 2.5 M.

5. The kit of claim 1, wherein the sodium chloride present in a concentration of about 2.0 M.

6. The kit of claim 1, wherein the epitope retrieval solution comprises sodium chloride.

7. The kit of claim 6, wherein the sodium chloride present in the epitope retrieval solution is present in a concentration of 0.5 to 3.0 M.

8. The kit of claim 7, wherein the sodium chloride present in the epitope retrieval solution is present in a concentration of 1.5 to 2.5 M.

9. The kit of claim 8, wherein the sodium chloride present in the epitope retrieval solution is present in a concentration of about 2.0 M.

* * * * *